United States Patent [19]

Thomas et al.

[11] 4,256,952

[45] Mar. 17, 1981

[54] DRAWER TYPE STERILIZER UNIT

[75] Inventors: Michael D. Thomas; Francis E. Ryder, both of Arab, Ala.

[73] Assignee: Ryder International Corporation, Arab, Ala.

[21] Appl. No.: 28,170

[22] Filed: Apr. 9, 1979

[51] Int. Cl.³ .............................................. A61L 2/04
[52] U.S. Cl. .................................. 219/521; 219/386; 219/401; 422/300; 422/307
[58] Field of Search ......................... 219/521, 385–387, 219/390–392, 399, 408, 433, 214, 219; 99/339, 371, 385, 393, 399; 34/201, 202; 312/236, 350, 300; 422/300, 307

[56] References Cited

U.S. PATENT DOCUMENTS

| | | | |
|---|---|---|---|
| 1,511,269 | 10/1924 | Decker | 219/218 |
| 1,983,491 | 12/1934 | Polhemus | 422/300 |
| 2,274,190 | 2/1942 | Cramer | 219/390 |
| 2,519,623 | 8/1950 | Baker | 312/350 |
| 2,961,284 | 11/1960 | Sturm | 312/350 |
| 3,087,771 | 4/1963 | Pari | 312/350 |
| 3,801,278 | 4/1974 | Wagner et al. | 422/300 |
| 3,983,362 | 9/1976 | Hoogesteger et al. | 126/275 E |
| 4,044,226 | 8/1977 | Kadlecik et al. | 126/275 E |
| 4,080,167 | 3/1978 | Beers | 219/385 |
| 4,165,359 | 8/1979 | Thomas et al. | 219/433 |

*Primary Examiner*—Elliot A. Goldberg
*Assistant Examiner*—Bernard Roskoski

*Attorney, Agent, or Firm*—Trexler, Wolters, Bushnell & Fosse Ltd.

[57] ABSTRACT

There is disclosed a contact lens disinfector unit for disinfecting contact lenses contained within a lens case. The disinfector unit includes a housing having a forward end wall and a rear end wall and a heating block within the housing. A resistive type heater is engaged with the block and is coupled to an electronic circuit and connector to adapt the unit for connection to a voltage source for causing the heating of a contact lens case in engagement with said block, and the contact lenses contained therein to a sterilizing temperature. The housing forward wall includes an aperture which slidingly receives a drawer having a pair of upstanding spaced apart panels and a contact lens case receiving aperture therebetween. The rear panel is disposed between the housing end walls and is greater in dimension than the forward wall aperture dimension to provide an abutment stop against the foward wall when the drawer is fully displaced from the housing, and also for preventing contact with the heating block and the voltage source connected thereto. The forward panel is also of greater dimension than the forward wall aperture for entirely enclosing the housing when the drawer is fully within the housing. The lens case receiving aperture of the drawer is arranged to be positioned above the heating block when the drawer is fully within the housing to provide surface contact between the undersurface of the lens case and the upper surface of the heating block during the sterilization cycle.

3 Claims, 6 Drawing Figures

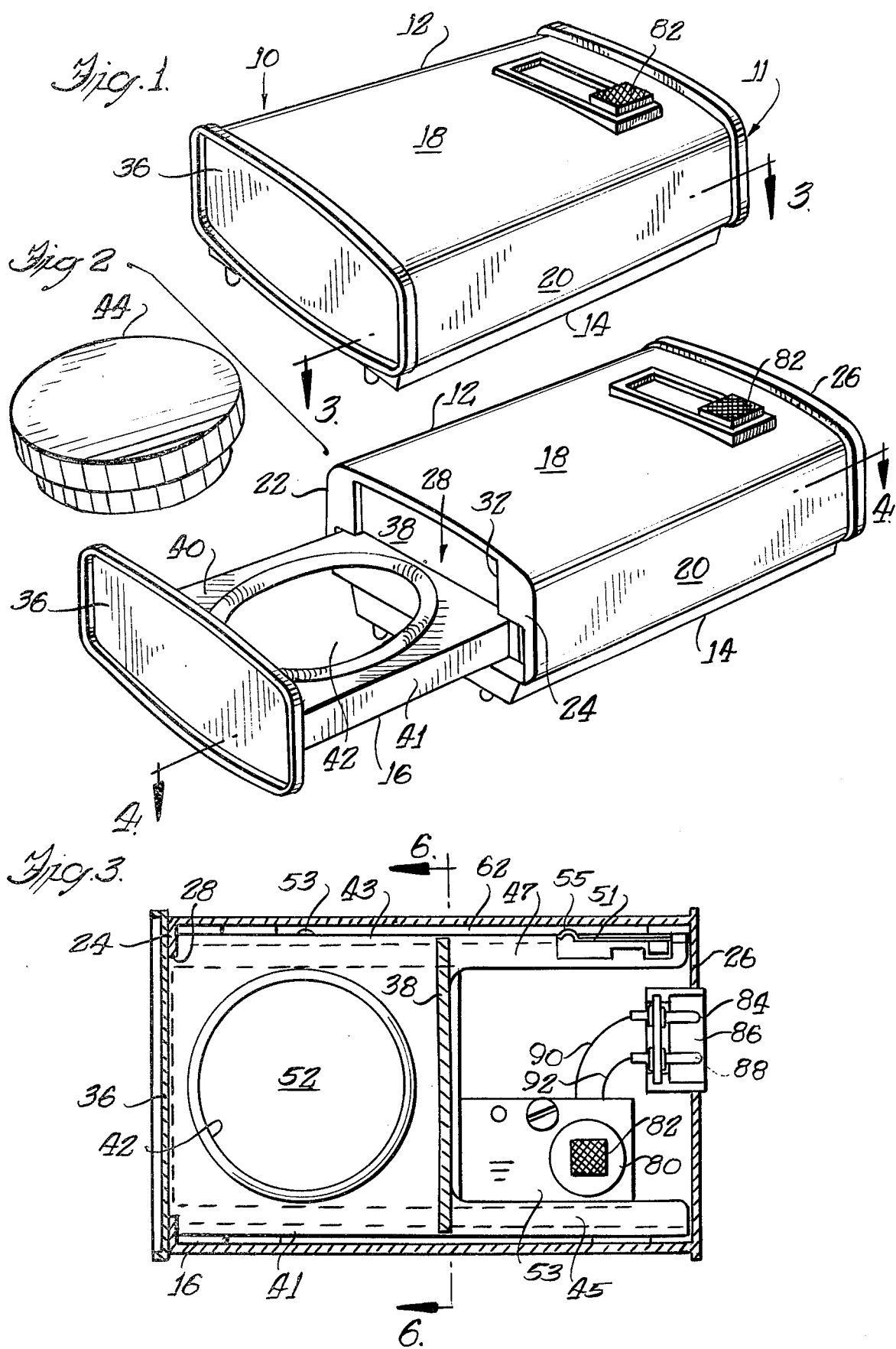

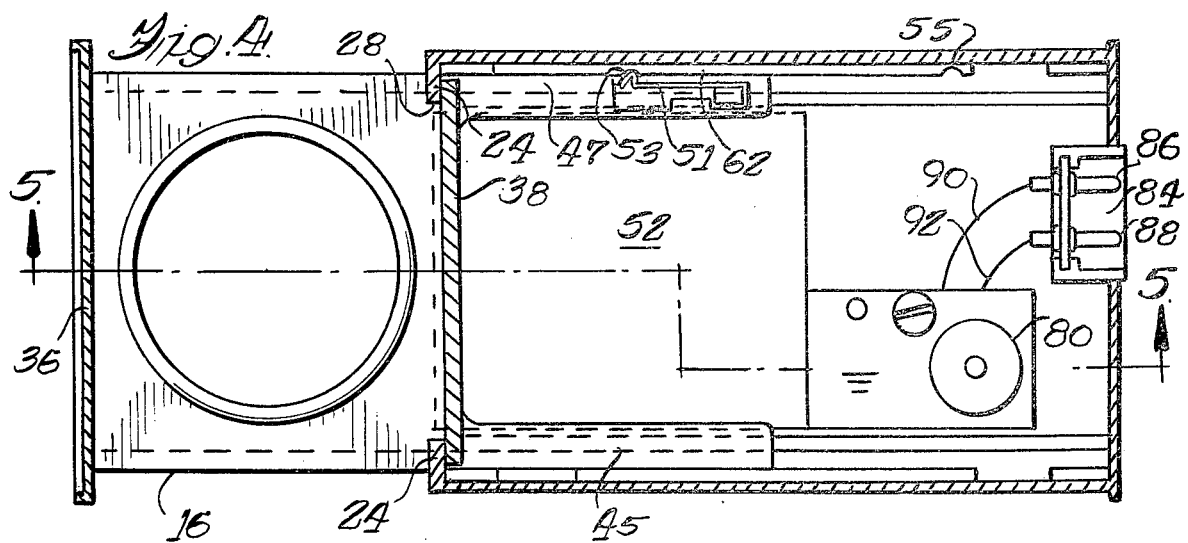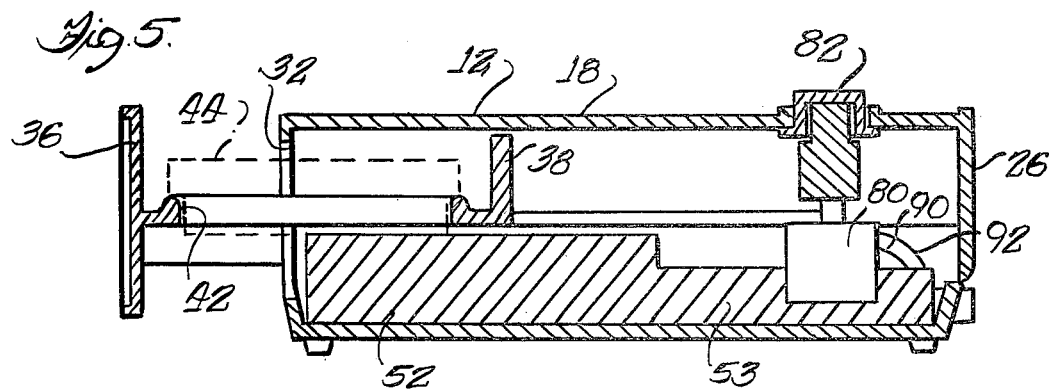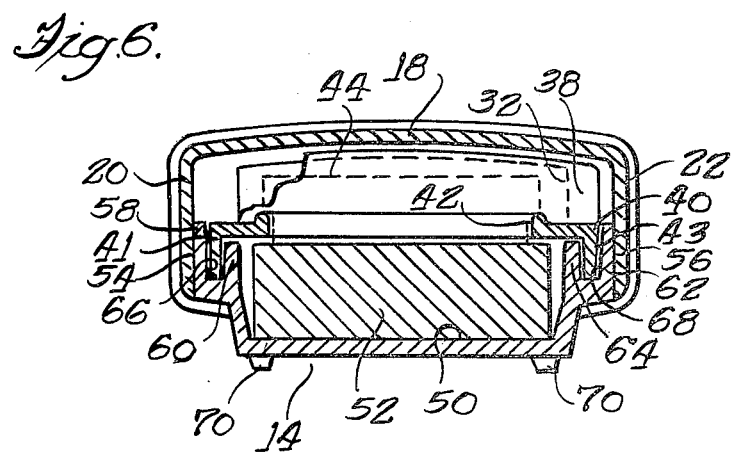

DRAWER TYPE STERILIZER UNIT

BACKGROUND OF THE INVENTION

The present invention is directed generally to a new and improved contact lens disinfector unit, and more particularly to an improved housing assembly construction for use in a contact lens disinfector unit which precludes contact with the unit heating block and the circuit components connected thereto.

Contact lenses, both of the hard and soft type, should be disinfected before use. To this end, a well accepted method of disinfecting is to dispose a pair of contact lenses in a container or lens case which may also have receptacles therein for holding the right and left lenses spaced apart so that they do not become confused. A quantity of disinfecting fluid is then administered to the container and the container is placed in engagement with a heating block of a disinfector unit for heating the disinfecting fluid to a prescribed temperature found to be sufficient to destroy harmful bacteria. The lens case is in direct contact with the heating block and the fluid within the container is in direct contact with the lenses and effects the disinfecting thereof. After the disinfecting temperature has been reached and maintained for a sufficient period of time, the lens case and the contact lenses contained therein are permitted to cool, preparatory to removal of the lenses from the case and disposition thereof on the eyes of a user.

In order to energize the unit, the heating block is associated with a resistive type heating element, which is connected to a suitable voltage source, such as a wall outlet for example, by a cord type connector and an electronic circuit contained within the disinfector unit housing. The circuit may include a thermostatic switch as a component thereof which, upon sensing that the heating block has reached a predetermined temperature, will open to break the circuit between the heating element and the voltage source. Because a voltage potential will still exist within the unit after operation of the thermostatic switch, which voltage is potentially injurious or even lethal in the case of infants or small children, care must be taken to prevent access to and contact with said circuit components.

It is therefore a general object of the present invention to provide a new and improved contact lens disinfector unit which includes a housing assembly designed and structured to preclude contact with the heating block and its associated circuitry which may carry potentially injurious voltage potentials.

It is a further object of the present invention to provide a housing assembly for use in a contact lens disinfector unit of the type which has a drawer slidingly received by an aperture in the housing to permit placement of a lens case into the drawer externally to the housing and wherein the drawer includes an upstanding panel which is of greater dimension than the aperture for providing an abutment stop when the drawer is fully displaced from the housing and for completely covering the drawer receiving aperture to prevent access to the interior of the housing and contact with the disinfector unit heating block and the associated heating circuitry.

The invention therefore provides a housing assembly for use in a contact lens disinfector unit of the type which disinfects a pair of contact lenses contained within a contact lens case. The unit includes heating means upon which the lens case rests and which is adapted to be connected to a voltage source for raising the lens case, and the contact lenses contained therein, to a temperature sufficient to attain disinfecting thereof. The housing assembly is specifically designed to prevent contact with the heating means from the exterior of the housing and includes a lower housing portion, an upper housing portion, the housing portions being adapted to interfit to form a structure having a pair of end walls, and aperture means within one of the end walls of a predetermined dimension. The housing assembly further includes a drawer means slidingly received within the aperture means, the drawer means having a pair of spaced apart upstanding panels or flanges, with a lens case receiving aperture between the panels. One of the upstanding panels is disposed interiorly of the housing, between the end walls, and is larger in dimension than the aperture means for providing an abutment stop against the one end wall when the drawer means is slidingly displaced with respect to the housing, the panel is sized and disposed with respect to the interior of the housing assembly to prevent contact with the heating means circuit components.

The invention further provides a contact lens disinfector unit comprising a housing having a lower housing portion and an upper housing portion defining a forward end wall and a rear end wall, heating means within the housing for heating a lens case containing contact lenses, connection means at the rear end wall for connecting the heating means to a voltage source, and aperture means within the forward end wall having a predetermined dimension. The disinfector unit also includes a drawer means slidingly received within the aperture means, wherein the drawer means has a pair of spaced apart upstanding panels and lens case receiving means between the panels. One panel is disposed between the end walls and is of larger dimension than the aperture means for providing an abutment stop against the forward end wall when the drawer means is slidingly fully displaced from the housing and for covering the aperture means to prevent contact with the heating means and voltage source connected thereto.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 1 is a perspective view of a contact lens disinfector unit embodying the present invention;

FIG. 2 is a perspective view of a contact lens disinfector unit of FIG. 1, with the drawer in the open condition for receiving a lens case containing the contact lenses to be disinfected;

FIG. 3 is a cross-sectional view taken along line 3—3 of FIG. 1;

FIG. 4 is a cross-sectional view taken along line 4—4 of FIG. 2;

FIG. 5 is a cross-sectional view taken along line 5—5 of FIG. 4 but with the disinfector unit shown in a partially open condition; and FIG. 6 is a cross-sectional view taken generally along line 6—6 of FIG. 3.

DESCRIPTION OF THE PREFERRED EMBODIMENT

Referring initially to FIGS. 1 and 2, the contact lens disinfector unit 10 as shown, includes a housing assembly 11 having an upper housing portion 12, a lower housing portion 14, and a lens case receiving drawer 16 slidably mounted to the housing assembly 11. The upper housing portion 12 is of a generally open-bottomed shell construction having a top panel portion 18, a pair of downturned side panels or walls 20 and 22, a forward end wall 24, and a rear end wall 26. The top panel 18, side walls 20 and 22, and end walls 24 and 26 are preferably integrally formed to result in an open bottomed, shell-like configuration for the upper housing portion 12.

The lower housing portion 14, which will be discussed in greater detail hereinafter is assembled to the upper housing portion 12, to close the bottom of the shell-like configuration provided by said upper portion 12. The forward end wall 24 includes an aperture portion 28, such when housing sections 12 and 14 are assembled, there is defined a complete or closed aperture with an upper portion 32 narrower than a lower portion 30 of said aperture 28.

As is best seen in FIGS. 2 and 5, the drawer 16 includes a pair of spaced upstanding panels or flanges, comprising a forward panel 36 and a rear panel 38. Between the panels 36 and 38 there is provided a horizontally disposed lens case carrier portion 40. Within the lens case carrier portion 40 is a lens case receiving aperture 42 which is dimensioned for receiving a lens case 44 of the type designed to accommodate a pair of contact lenses and a quantity of disinfecting solution. The contact lens case receiving aperture 42 is between the panels 36 and 38, and as can be seen is so positioned that when the drawer 16 is fully within the disinfector unit housing, as shown in FIG. 3, the aperture 42 will be spaced above a heating block 52 to enable the case 44 to be disposed in surface contact with the heating block. Further, the drawer 16 includes a pair of spaced or bifurcated arms or extensions, 45 and 47 (FIG. 3) which extend rearwardly from the panel 38.

The drawer 16 and the lens case carrier portion 40 are sized and dimensioned for sliding reception in the lower portion 30 of aperture 28. The rear panel 38 on the drawer 16 is of greater dimension than the upper portion 32 of the aperture 28, such that the portion of wall 24 defining the upper aperture portion 32 provides an abutment or stop, against which the panel 38 will engage when the drawer 16 is fully displaced, as shown in FIGS. 2 and 4, thus preventing removal of said drawer. In this condition, the panel 38 completely overlies the upper portion 32 of aperture 28, such that said panel 38 and the drawer 16 effectively fill the entire aperture 28 to preclude access to the interior of the disinfector unit, and contact with the circuit components therein.

The forward panel 36 is greater in dimension than the aperture 28 and is dimensioned in general correspondence to the peripheral dimension of the upper housing portion 12. As a result, when the drawer 16 is fully within the disinfector unit as shown in FIG. 1, the forward panel 36 entirely overlies the end wall 24 and closes the aperture 28 during the heating operation to disinfect the contact lenses.

The construction of the lower casing portion 14 will now be considered, as will the interior construction of said housing 11. In this regard, initial reference is directed to FIG. 6, where it can be seen that the lower housing portion 14 includes a generally central cavity 50, in which is disposed a heating block 52 formed from metallic material, and the necessary circuit components. The lower housing portion 14 also includes a pair of upstanding elongate flanges 58 and 60 extending along one lateral edge, and a second pair of flanges 62 and 64 extending along the other lateral edge, to form a pair of substantially parallel recessed tracks 66 and 68. The flanges 58 and 62 have outer surfaces 54 and 56 respectively against which the sidewalls 20 and 22 respectively are interfitted in juxtaposed position. Lastly, the lower housing portion 14 includes a plurality of feet 70 which serve to space the disinfector unit above a support surface and prevent damage thereto due to excessive heat.

With the above in mind, it should be noted that the lens case tray 16 has a pair of substantially parallel downturned edge flanges 41 and 43 which are spaced apart and dimensioned so as to be received within the recessed tracks 66 and 68, respectively. As a result, the drawer 16 is confined laterally, yet is arranged for horizontal sliding movement longitudinally with respect to the disinfector unit housing 11.

Referring now to FIG. 3, it can be seen that the drawer 16 includes a pair of bifurcated extensions 45 and 47, in addition to panels 36 and 38, and the lens case carrier portion 40. The extensions 45 and 47 extend rearwardly from panel 38 and include portion of the downturned flanges 41 and 43. By virtue of this structure, the drawer 16 finds continuous support within the disinfector unit housing with the drawer 16 in the extended or open condition. In the illustrated, preferred embodiments, the extension 47 carries a spring member 51, which co-acts with a pair of detents 53 and 55 within the ridge 62 for releasably locking the drawer in position when fully closed and when fully open. The spring member 51 engages the detent 55 when the drawer is fully closed as seen in FIG. 3, and engages the detent 53 when fully open as seen in FIG. 4.

Disposed within the disinfector unit 10 and supported by the lower housing portion 14 is the heating block 52. The heating block 52 has a rearward extension 53 which carries a thermostatic switch 80 of generally known design. The thermostatic switch 80 has a reset button 82 which, as can be best seen in FIGS. 1, 2 and 5, extends through the top panel 18. When reset button 82 is depressed, the heating element (not shown) in engagement with the heating block 52 is placed in circuit to actuate the disinfecting unit. Once the heating block 52 reaches the desired, predetermined temperature for disinfecting the lens, the thermostatic switch 80 will be actuated to break the circuit to the heater element, thereby permitting the unit to cool, with disconnection from the power source. As can be appreciated, this feature enables disinfecting to take place at night, while a user is sleeping, or otherwise will need for continuous monitoring.

Carried by the rear end wall 26 of the housing 11 is an electric connector 84 having a pair of connecting pins 86 and 88 connected in circuit with the thermostatic switch 80 by a pair of leads 90 and 92. The connector 84 adapts the disinfector unit for connection to an external voltage source such as a wall outlet by means of a conductor cord. Thus, keeping in mind the above discussion concerning operation of the thermostatic switch 80, even though the unit has cooled, the voltage potential provided by a wall outlet is still present and is potentially injurious upon human contact. Hence, the disinfector unit of the present invention is constructed to prevent access to the circuitry of the heating arrangement wherein said voltage potential exists.

Referring now to FIG. 3, it can be seen that when the disinfector unit drawer 16 is fully within the disinfector unit housing, the forward panel 36 of the drawer 16 overlies the end wall 24 and entirely closes the aperture 28, such that access to the interior of housing 11 is precluded. As can be seen in FIGS. 2 and 4, when the drawer 16 is fully displaced from the disinfector unit, the rear panel 38 and the associated portion of the drawer 16 entirely fill the aperture 28, preventing access to the interior of the housing. More specifically, as can be seen in FIG. 2, the rear panel 38 entirely overlies the upper portion 32 of the aperture 28. As a result, contact with the heating block 52, and more importantly, the internal circuitry is precluded. Also, as mentioned previously, the rear panel 38 forms an abutment stop against the forward end wall 24 to limit the horizontal displacement of the drawer 16, such that said drawer 16 cannot be removed; which removal, if effected, would afford access to the interior circuitry.

Referring now to FIGS. 5 and 6, in FIG. 5 an intermediate position of drawer 16 is shown. It can be seen that the side walls 20 and 22 of the upper section 14 are closely adjacent the recess tracks 66 and 68 and the corresponding vertical edges of the panel 33. More specifically, the panel 38 is dimensioned such that vertical edges thereof are closely adjacent the side walls 20 and 22, and also the top edge of the panel 38 is closely spaced from the top panel 18 of the upper housing portion 12. As a result, the panel 38 precludes access to the rearward portion of the disinfector unit housing where the potentially injurious voltage potentials exist, even though the drawer 16 is in the partially open position.

The present invention therefore provides a new and improved drawer type disinfector unit that precludes access to the interior of the disinfector unit in all positions of the drawer. Furthermore, the rear panel carried by the drawer provides an abutment stop to preclude removal of the drawer. Because access to the interior of the disinfector unit is precluded, injurious contact with the voltage potentials utilized by the heating block and carried by the circuitry associated with the heating block is obviated.

While a particular embodiment of the present invention has been shown and described, modifications may be made and it is therefore intended to cover all such changes and modifications which fall within the spirit and scope of the invention, as defined by the claims appended hereto.

The invention is claimed as follows:

1. A contact lens disinfector unit of the type designated to receive a lens case having a pair of contact lenses immersed within a disinfecting solution disposed within said case, wherein said disinfector unit is adapted to heat said disinfecting solution to an elevated temperature thereby to asepticize said lenses, said disinfector unit comprising: a housing having an open end wall and track means disposed internally of said housing; electrical resistent heating means carried within said housing and including an electrically heated heating block having a generally planar upper surface; and drawer means slidably mounted with respect to the track means on the interior of said housing and received within said open end wall, said drawer means including a generally planar section having through aperture formed therein and an upstanding panel on the free end of said drawer means said drawer means being movable between an extended position wherein said aperture generally planar section projects from said housing and said through aperture is disposed for receiving a lens case, and a retracted position, wherein said planar section is received within said housing with said through aperture being superposed of said planar upper surface of the heating block, a lens case disposed in said aperture with the base portion of said lens case exposed for engagement with said heater block upper surface, and said up-standing panel being sized such that when drawer means is in the retracted position, said panel will close the end wall of said housing.

2. A contact lens disinfector unit according to claim 1, wherein said drawer means further includes a second up-standing panel disposed on the opposite side of said lens case receiving through aperture from said first mentioned panel, said second panel being disposed within said housing and of a larger dimension than the opening in said open end wall, thereby providing an abutment stop against said end wall when said drawer means is in the extended position, said panel also being of sufficient size to preclude contact with said electrical resistance heater means through the open end wall of said housing when said drawer means is in the extended position.

3. A contact lens disinfector unit as defined in claim 1 wherein said housing includes a pair of spaced apart side walls, one of said side walls including a pair of spaced apart detents, and wherein said drawer means includes a spring member arranged to engage said detents for releasably locking said drawer means when fully displaced from said housing and when fully disposed within said housing.

* * * * *